(12) United States Patent
Schuster

(10) Patent No.: US 11,118,174 B2
(45) Date of Patent: Sep. 14, 2021

(54) DEVICE AND METHOD FOR ISOLATING NUCLEIC ACIDS FROM WHOLE BLOOD

(71) Applicant: SARSTEDT AG & CO. KG, Nuembrecht (DE)

(72) Inventor: Rainer Schuster, Nuembrecht (DE)

(73) Assignee: SARSTEDT AG & CO. KG, Nümbrecht (DE)

( * ) Notice: Subject to any disclaimer, the term of this patent is extended or adjusted under 35 U.S.C. 154(b) by 0 days.

(21) Appl. No.: 16/077,123

(22) PCT Filed: Feb. 10, 2017

(86) PCT No.: PCT/EP2017/053025
§ 371 (c)(1),
(2) Date: Dec. 19, 2018

(87) PCT Pub. No.: WO2017/137573
PCT Pub. Date: Aug. 17, 2017

(65) Prior Publication Data
US 2019/0127729 A1    May 2, 2019

(30) Foreign Application Priority Data

Feb. 11, 2016 (EP) .................................. 16155286

(51) Int. Cl.
| C07H 1/06 | (2006.01) |
| C12N 1/06 | (2006.01) |
| C12Q 1/6806 | (2018.01) |
| C12N 15/10 | (2006.01) |

(52) U.S. Cl.
CPC ........... *C12N 15/1013* (2013.01); *C07H 1/06* (2013.01); *C12N 1/06* (2013.01); *C12N 15/1006* (2013.01); *C12Q 1/6806* (2013.01)

(58) Field of Classification Search
None
See application file for complete search history.

(56) References Cited

U.S. PATENT DOCUMENTS

| 2003/0219788 A1* | 11/2003 | Kaltenboeck .... C12Q 2531/113 |
| | | 435/6.12 |
| 2006/0105372 A1* | 5/2006 | Bair .................. C12N 15/1006 |
| | | 435/6.18 |
| 2016/0032277 A1 | 2/2016 | Ambros et al. |
| 2016/0348151 A1* | 12/2016 | Wyrich ................ C12Q 1/6841 |

FOREIGN PATENT DOCUMENTS

| CA | 2348152 A1 | 2/2002 |
| CN | 103820431 | 5/2014 |
| CN | 103820431 A | 5/2014 |
| CN | 104673623 A | 6/2015 |
| DE | 10147439 A1 | 4/2003 |
| DE | 102014220090 B3 | 10/2015 |
| EP | 3389063 A2 | 9/1990 |
| WO | 0009746 | 2/2000 |
| WO | 02056030 A2 | 7/2002 |
| WO | 2006052680 A1 | 5/2006 |
| WO | 2007060248 A1 | 5/2007 |
| WO | 2009018034 A1 | 2/2009 |

OTHER PUBLICATIONS

Bassias, International Search Report for Application No. PCT/EP2017/053025, dated Mar. 24, 2017.
Japanese Office Action from the corresponding Japanese Patent Application No. 2018-561307, dated Sep. 4, 2020.

* cited by examiner

*Primary Examiner* — Katherine D Salmon
(74) *Attorney, Agent, or Firm* — Greer, Burns & Crain, Ltd.; Steven P. Fallon

(57) ABSTRACT

The invention relates to a composition for stabilizing the total nucleic acids from whole blood, in particular RNA, and to a process for stabilizing the total nucleic acids from whole blood for subsequent isolation and at the same time serves for the disruption of cells so that cellular nucleic acids in the state at contacting the composition, especially at the point of time of blood collection, are released and are maintained stable in respect of quality and concentration and can be isolated subsequently. Therein, the composition is characterized in that it especially prevents the degradation and new synthesis of RNA in whole blood, into which it is mixed. The isolation of RNA by contacting the mixture of the aqueous composition and blood with an adsorption agent can be made directly from the complete mixture of the aqueous composition with blood, i.e. e.g. without precipitation and separation of nucleic acids from the mixture, optionally after a storage, during which the mixture is e.g. transported from the place of blood collection to the place of the analytical process.

15 Claims, No Drawings

DEVICE AND METHOD FOR ISOLATING NUCLEIC ACIDS FROM WHOLE BLOOD

The present invention relates to a composition and to a process for stabilizing nucleic acids, especially RNA, including the RNA contained in cells, from a biological sample, especially from whole blood, preferably with the subsequent isolation of nucleic acids, as well as to a device for use as a blood collection tube that contains the composition which is suitable for stabilizing the total nucleic acids, especially the total RNA, and for the subsequent isolation.

The composition for stabilizing the nucleic acids from a biological sample, especially whole blood, the process and the blood collection tube usable for the process and containing the composition, are characterized in that an effective stabilization of nucleic acids, especially of RNA, is achieved in whole blood and allows for a fast and effective process for isolation. Therein, the stabilization comprises the total nucleic acids, especially the total RNA, including the nucleic acids contained in the cell free plasma, especially RNA, and the nucleic acids, especially RNA, contained in the cells present in blood.

STATE OF THE ART

WO 02/056030 A2 for stabilization of the content of RNA in a sample describes a container having a predetermined vacuum for drawing in a predetermined sample volume, wherein in the container an agent is provided for inhibiting gene induction and against the enzymatic degradation of nucleic acids, especially mercapto ethanol, dithiotreitol (DTT) and a chaotropic salt, especially guanidinium isothiocyanate or guanidinium hydrochloride.

WO 00/09746 A1 describes a vessel for blood collection that contains a solution of a guanidinium salt, buffer, detergent and a reducing agent, especially DTT, β-mercapto ethanol und TCEP (tris(2-carboxyethyl)phosphine) for lysis of cells and for stabilizing nucleic acids. The reducing agent, especially β-mercapto ethanol or DTT, therein is regarded as essential for stabilizing RNA in serum.

WO 2009/018034 A1 relates to the increase of the solubility of SDS in lysis buffer for cells by adding a nonionic detergent and to a process for isolating DNA from animal tissue by addition of a lysis buffer of 2M NaCl, 1.2% SDS, 12 mM EDTA, 24 mM Tris-HCl, pH 8.0 with 2% Tween and subsequent addition of the ten-fold volume of an extraction buffer of 50 mM Tris-HCl, pH 7, 10 mM EDTA, 7 M guanidin-HCl, 5% Tween20.

WO 2007/060248 A1 is directed to the lysis of cells, namely liver tissue, with chaotropic salt and subsequent addition of a non-chaotropic salt for binding nucleic acids to a carrier material.

DE 101 47 439 A1 for isolation of DNA from blood describes that a lysis reagent is added and DNA-containing cell components are subsequently separated by centrifugation. The sedimented DNA is purified by resuspending it with guanidinium hydrochloride and separating impurities, e.g. protein, and is precipitated by addition of alcohol and separated.

DE 10 2014 220 090 B3 for collecting biological samples containing nucleic acids describes a vessel into which is swab can be introduced, the vessel containing a lysis liquid.

CN 104673623 A according to the English language abstract describes a sample vessel having a lid for stabilizing hematocyte nucleic acids and cell-free DNA.

OBJECT OF THE INVENTION

It is an object of the invention to provide an alternative composition and preferably an alternative process for stabilization and for subsequent isolation of the total nucleic acids from whole blood. Preferably, the composition shall stabilize the total RNA of whole blood and allow a quick process for isolating the total nucleic acids, especially RNA. Further preferred, the composition shall allow the stabilization of nucleic acids for a variable blood volume, so that a blood collection tube containing the composition need not be adapted necessarily to draw in a predetermined blood volume.

DESCRIPTION OF THE INVENTION

The invention achieves the object by the features of the claims, especially by a composition for stabilizing the total nucleic acids from whole blood, especially of RNA, and by a process for stabilizing the total nucleic acids from whole blood for subsequent isolation and concurrently serves cell disruption, so that cellular nucleic acids are released in the state of contacting the composition, especially at the point of time of blood sampling and are maintained as stable in respect of quality and concentration and can be isolated subsequently. Therein, the composition is characterized in that it prevents especially the degradation and the new synthesis of RNA in whole blood, into which it is mixed. Accordingly, the invention relates to the use of the composition, preferably contained in a blood collection tube, for the process, especially as an agent for stabilizing and isolating the total RNA of blood without the step of precipitating and separating of RNA prior to adsorption of RNA to an adsorption agent. For isolation, the mixture of blood and of the aqueous composition can be contacted with an adsorption agent without precipitating the RNA. The isolation of RNA by contacting the mixture of the aqueous composition and blood with an adsorption agent can occur directly from the complete mixture of the aqueous composition with blood, i.e. for example without precipitating and separating nucleic acids from the mixture, optionally following a storage during which the mixture is transported e.g. from the place of taking a blood sample to the place of the analytical process.

The biological sample preferably is liquid and optionally contains human, respectively animal cells. The biological sample can e.g. be a body fluid, e.g. liquor, urin, sputum, a biopsy having a content of separated or homogenized cells and especially whole blood, also termed blood. The description representatively relates to whole blood as biological samples.

The composition in aqueous solution comprises or consists of
at least one guanidinium salt, preferably guanidinium thiocyanate,
at least one buffering agent, preferably 2-(N-morpholino) ethanesulfonic acid (MES),
a non-ionic detergent, preferably Triton X-100, and
a complexing agent for divalent cations, preferably ethylene diamine tetraacetate (EDTA), and is especially free from reduction agents, e.g. free from thiol compounds or their precursor compounds, especially free from β-mercapto ethanol and dithiothreitol (DTT).

In an aqueous solution, the composition contains
the at least one guanidinium salt, e.g. to 1.8 to 2.6 M, preferably 2.0 to 2.4 M, more preferred 2.2 M,
the least one buffering agent in a concentration which buffers a blood volume to a pH of from 5.0 to 8.0, e.g. from pH 5.1, 5.2, 5.3, 5.4, 5.5, 5.6, 5.7, 5.8, 5.9 or 6.0 to 7.5, 7.6, 7.7, 7.8, 7.9, preferably pH 6.5 to 7.3, e.g. MES to at least 50 mM, preferably at least 70 mM, e.g. up to 100 mM or up to 74 mM, the non-ionic detergent, e.g. Triton X-100, to 10-20% wt/vol, preferably 12 to 18% wt/vol, a complexing agent for divalent cations, especially EDTA, e.g. from 50 to 100 mM, preferably 70 to 80 mM, more preferred ca. 72 mM, e.g. for a blood volume up to a ratio to the volume of the aqueous composition of 1:13 or 1:3 or up to 1:2, preferably up to 1:2.6 or up to 1:2.5 or 1:2.4, or consists thereof.

Preferably, the invention relates to the composition for use as a disruption agent for cells contained in a biological sample, especially in whole blood, as a stabilizating agent for the total nucleic acids of the biological sample, and for isolating the nucleic acids by means of adsorption from a mixture of the biological sample with the composition to an adsorption agent for nucleic acids, wherein the composition in aqueous solution contains
 a. at least one guanidinium salt,
 b. at least one buffering agent for buffering to a pH of from 5.0 to 8.0,
 c. at least one non-ionic detergent and
 d. at least one complexing agent for divalent cations and
 e. is free from reducing agents.

Preferably, the composition consists of an aqueous solution of
 a. the at least one guanidinium salt,
 b. the at least one buffering agent,
 c. the at least one non-ionic detergent and
 d. the at least one complexing agent,
  and optionally proteinase and/or DNase.

The composition finds use as a disruption agent for cells contained in whole blood and as a stabilizing agent for the total nucleic acids contains therein and for isolating by adsorption of the nucleic acids directly out of a mixture of the biological sample and the composition to an adsorption agent for nucleic acids.

The buffering agent is e.g. selected from Tris (tris(hydroxy methyl)-aminomethane), citrate or phosphate (disodium hydrogenphosphate)dihydrate, respectively phosphate(sodium hydrogenphosphate)dihydrate, BisTris buffer (bis-(2-hydroxy methyl)-imino-tris-(hydroxy methyl)-methane), ACES (N-(2-acetamido)-2-amino methane sulfonic acid), sodium hydrogencarbonate, preferably 2-(N-morpholino)ethanesulfonic acid (MES).

The non-ionic detergent is e.g. selected from Tween20 (polyoxyethylene(20)-sorbitanmonolaurate), Nonidet P40 (4-nonylphenol-polyethylene glycol), Tween80 (polyoxy ethylene sorbitane monooleate), Brij 58 (polyethylene glycol-hexadecylether), Triton X-114 (octylphenol polyethylene glycolether), preferably Triton X-100 (polyethyleneglycol-p-(1,1,3,3-tetra methylbutyl)phenylether).

The composition has the advantage to lyse the human cells contained in whole blood and to stabilize the total nucleic acids, especially RNA, of whole blood, wherein whole blood and the composition can be present in a variable volumetric ratio. A blood collection tube containing the composition can therefore be arranged to draw in a variable volume of blood, e.g. the blood collection tube can be arranged to draw in blood up to a volumetric ratio of 1:13 or 1:3, preferably up to 1:2 or up to 1:2.6 in relation to the composition. For drawing in a variable volume of blood the blood collection tube in which the composition is contained can e.g. have a piston which is manually retractable out of a tube.

The composition is characterized in that it does not require the precipitation of the nucleic acids from the mixture of whole blood and the composition in order to stabilize and to isolate the nucleic acids, especially RNA, from the whole blood. Therefore, the process according to the invention preferably contains the isolation of nucleic acids, especially of RNA, from the mixture of whole blood and the composition without a step of precipitating nucleic acids, especially RNA, respectively without a step of centrifugation for separating precipitated nucleic acids prior to the binding of nucleic acids, especially of RNA, to an adsorption agent.

According to the invention RNA is preferably isolated from the mixture of whole blood and the composition by contacting the mixture of whole blood and the composition with an adsorption agent for nucleic acids, optionally following the addition of proteinase, e.g. of Proteinase K, and incubating, e.g. at room temperature for ca. 15 min, optionally adding of DNase prior to or subsequent to adding of the proteinase, wherein from the mixture, optionally including added proteinase and/or DNase, prior to contacting with the adsorption agent, no ingredient is separated, subsequently the compounds not bound to the adsorption agent are separated, e.g. by washing the adsorption agent, and nucleic acids that are bound to the adsorption agent are eluted, e.g. by contacting the adsorption agent with an aqueous buffer having a pH value, a content of alcohol and/or ionic concentration that releases bound nucleic acids.

The mixture of whole blood and the composition can be contacted completely with the adsorption agent for nucleic acids and in time directly after producing the mixture. This results in the advantage that the process for isolating the nucleic acids, especially RNA, does not require an incubation for precipitation and no centrifugation prior to contacting the mixture with the adsorption agent and no addition of further compounds, and can therefore be performed simply and quickly.

Following the contacting of the mixture of whole blood and the composition, which optionally contains added proteinase, optionally DNase can be added, so that DNA is digested and essentially RNA is isolated.

The adsorption agent for nucleic acids for example is a silica surface, especially silica(gel)membrane, silica(gel) suspension, or silica-coated magnetic particles, e.g. such as obtainable for isolating nucleic acids under the designation PAXgene from the company PreAnalytiX, under the designation NucleoSpin from the company Macherey-Nagel, under the designation mRNA Isolation Kit for Blood/Bone Marrow or under the designation High Pure Viral Nucleic Acid Large Volume Kit of the company Roche.

In case the adsorption agent consists of silica-coated particles, preferably magnetic particles, it is preferred to add a thinner in an effective volume to the mixture of whole blood and the composition. The thinner can e.g. be the DNA/RNA stabilization reagent for Blood/Bone marrow obtainable from the company Roche (Roche article number 11 934 317 001) or the composition according to the invention, in each case optionally with a content of up to 30 vol./vol.-% ethanol, preferably 10 to 30 vol./vol.-% ethanol, e.g. 20 vol./vol.-% ethanol. An effective volume can be determined as one for which the RNA is adsorbed to the silica-coated particles essentially to at least 80% of the total amount, preferably essentially completely. The effective volume at which the thinner is added to the mixture of whole blood and the composition preferably amounts to 50 to 150% of the volume of the mixture, e.g. 80 to 120%, preferably 100% of the volume of the mixture, added prior to or following admixing of the silica-coated particles into the mixture, which preferably are magnetic particles. Especially in this embodiment, the addition of proteinase to the mixture is preferred.

Silica-coated particles can e.g. be those from the company Chemagen or the company Applied Biosystems (RNA binding beads, article number 100191) or from the company Roche from the mRNA Isolation Kit for Blood/Bone Marrow, article number 11 934 333 001 or those according to Hai N. H., Phu N. D., Luong N. H., Chau N., Chinh H. D., Hoang L. H., Leslie-Pelecky D. L. (2008), Mechanism for Sustainable Magnetic Nanoparticles under Ambient Conditions, *Journal of the Korean Physical Society*, 52 (5), 1327-1331 or those according to Quy D. V., Hieu N. M., Tra P. T., Nam N. H., Hai N. H., Son N. T., Nghia P. T., Anh N. T. V., Hong T. T., Luong N. H. (2013) Synthesis of Silica-Coated Magnetic Nanoparticles and Application in the Detection of Pathogenic Viruses, *Journal of Nanomaterials*, DOI: 10.1155/2013/603940.

The complete mixture of whole blood and of the composition is contacted with the adsorption agent with the thinner added also for an adsorption agent of silica-coated particles, which preferably are silica-coated magnetic particles, i.e. directly, respectively, completely, respectively without prior separation of a component from the mixture.

According to the invention, the complete mixture can be contacted directly with the adsorption agent, because from the mixture of whole blood and the composition no component, respectively, no fraction is separated off, especially no centrifugation of this mixture for separating a precipitated ingredient, e.g. no centrifugation of precipitated nucleic acids with subsequent separating the liquid phase and dissolving of the nucleic acids is necessary. Presently, this is attributed to the composition not precipitating nucleic acids, especially RNA, in the mixture with whole blood. In contrast, the composition has the advantage that a mixture of whole blood and of the composition, optionally with proteinase and/or DNase added, without further treatment steps, respectively without additives, can be contacted with an adsorption agent for nucleic acids, especially silica surfaces, in order to bind the nucleic acids to the adsorption agent. Therefore, the composition allows a process for isolating nucleic acids which is performed without separation of a fraction containing nucleic acids prior to the contacting with the adsorption agent, e.g. without precipitation by means of centrifugation and subsequent dissolving.

The compositions stabilizes the nucleic acids, especially RNA, in the mixture of whole blood and of the composition, e.g. during a storage for at least 3 days, preferably for at least 5 days, e.g. for up to 4 days, especially without freezing, e.g. storage at at least 0° C., e.g. at room temperature up to 22.5° C. Correspondingly, the process preferably contains the isolation of nucleic acids, especially of RNA, from the mixture, e.g. subsequent to a storage without freezing, respectively at at least 0° C., e.g. at 15 to 25° C., especially at up to 22.5° C. Alternatively, or additionally, the mixture can be frozen, e.g. at −40° C. or below, for storage.

The invention is now described in greater detail by way of examples with relation to the figures, which show in FIG. 1 the integrity of RNA that was isolated from whole blood in mixture with a composition according to the invention in different volumetric ratios, FIG. 2 the concentration of the RNA which was isolated from whole blood in mixture with a composition according to the invention at different volumetric ratios, FIGS. 3 and 4 the comparison of the RNA integrity of whole blood samples (Do. 1, donor No. 1, and Do. 2, donor No. 2) after storage in a stabilizer according to WO 00/09746 in comparison to a storage in a composition according to the invention, FIG. 5 a cluster analysis of the concentration of different mRNAs in the total RNA which was isolated from whole blood in mixture with a composition according to the invention, FIG. 6 a correlation matrix for depicting differences in expression in dependence from storage, FIGS. 7 and 8 the relative amounts of mRNAs determined by means of RT-PCR in samples of two donors, which were isolated subsequent to storage of the whole blood for 5 days in mixture with a composition according to the invention.

The composition according to the invention was provided as an aqueous solution in a blood collection tube into which a blood sample was drawn. The blood collection tube can be used directly for sampling of blood. Alternatively, the composition can be mixed with whole blood, which preferably originates from a sample of whole blood collected immediately previously. The destruction of cells of the blood sample and the stabilization of the nucleic acids, especially of the RNA, generally occurs by mixing the whole blood sample with the composition.

EXAMPLE 1: ISOLATING OF RNA FROM WHOLE BLOOD

As a composition according to the invention, an aqueous solution was used which consisted of 2.2 M guanidinium thiocyanate, 72 mM MES, 14.4% (wt./vol.) Triton X-100 and 72 mM EDTA in water. From this composition, 6.5 mL were contained in a conventional blood collection tube into which blood was drawn that was collected immediately previously and which was not treated any further and did not contain any additive. This whole blood was drawn in a volume of 0.5 mL, 1.0 mL, 1.5 mL, 2.0 mL and 2.5 mL into respectively one blood collection tube. The mixing occurs by drawing in the blood volume, optionally additionally by shaking, especially following drawing in of an air bubble.

The mixture of the composition and whole blood was provided with Proteinase K (250 µL, 18 µg/mL). The mixture was incubated for approximately 15 min at room temperature. Subsequently, the mixture was completely put through a column containing an adsorption agent (High Pure Viral Nucleic Acid Large Volume Kit, obtainable from Roche) for nucleic acids. The adsorption agent was washed with washing buffer according to the instructions of the manufacturer, subsequently the bound nucleic acids were eluted with 100 µL elution buffer.

The quality of the eluted RNA was evaluated by means of electrophoresis in an RNA Nano Chip System (Agilent Technologies, USA), detection was by means of an Agilent 2100 Bioanalyser, wherein a so-called RIN is given as a measure for the RNA integrity, which is determined in the analysis by means of the Bioanalyser 2100. FIG. 1 by way of the result of the analysis for the different volumetric ratios of whole blood and composition (RNA Exact) shows that the RNA integrity does not depend on the volumetric ratio, respectively that the composition stabilizes RNA of equal quality for different volumetric ratios with whole blood and that the RNA can be isolated from their mixture.

FIG. 2 shows the RNA concentration measured in eluate, which were isolated for the different volumetric ratios. By way of the RNA concentrations in 100 µL eluate, the results show by way of the RNA concentrations increasing in proportion to the blood volume that the composition (RNA Exact) for the different volumetric ratios stabilizes RNA to the same extent and RNA is isolated therefrom to the same extent. This shows that the composition is suitable for the lysis of cells in whole blood and for the stabilization of the nucleic acids in whole blood in different volumetric ratios.

EXAMPLE 2: COMPARISON OF THE STABILIZATION PERFORMANCE OF THE COMPOSITION ACCORDING TO THE INVENTION TO A COMPARATIVE SOLUTION

As a composition according to the invention (RNA Exact) the one of Example 1 was used at resp. 6.5 mL and mixed with 2.5 mL of blood that was collected directly before, which did not contain any other additives, in order to produce the mixture of the composition and whole blood. For comparison a solution was used that consisted of 4.0 M guanidinium thiocyanate, 45 mM Tris/HCL, 18.0% (wt./vol.) Triton X-100 und 0.8% (wt./vol.) DTT in water and was adjusted to a pH of 6.0 (comparison according to WO 00/09746 A1). 2.5 mL of the comparative solution were mixed also with 2.5 mL of the directly previously collected blood sample as described in WO 00/09746 A1 (ratio 1+1). The mixtures were stored at 22.5° C. and the RNA was collected from the mixtures by NucleoSpin RNA Blood Midi Kit of the company Macherey-Nagel. As provided for in the protocol by Macherey-Nagel, ⅓ of the volume in 70% ethanol was added to the comparative solution. This is not necessary for the mixture with the composition according to the invention. FIG. 3 and FIG. 4 show the results of the capillary electrophoretic separation of the eluates on an RNA-Nano-Chip in the Bioanalyser 2100. Whereas from the sample mixture with the composition according to the invention RNA having a high integrity could be isolated also after 3 days and after 5 days, when using the comparative solution this is only possible on day 0, that is directly after the mixing with blood.

EXAMPLE 3: STABILIZATION OF RNA FROM WHOLE BLOOD AND ISOLATION

The composition according to claim 1 was used as the one according to the invention, each at 6.5 mL, and mixed with 2.5 mL of blood that was collected directed previously, which did not contain any other additives, in order to produce the mixture of the composition and whole blood. For comparison, blood was drawn into blood collection tubes that contained EDTA for inhibiting coagulation (S-Monovettes EDTA-K3, obtainable from the company Sarstedt). The blood originated from three different donors each.

The mixtures according to the invention and the comparative samples were incubated at 22.5° C., wherein one aliquot was immediately taken (T0, day zero), after 1 day of incubation (T1) and after 3 days of incubation (T3). From the aliquots taken, nucleic acids were directly and immediately isolated as described in Example 1.

The eluted nucleic acids were treated with DNase (Thermo Fisher Scientific, article number EN0521) for removing DNA and were tested by means of a microarray analysis for the concentration of ca. 47000 transcripts (mRNA) (humanHT-12 v4.0 Expression Bead Chip from the company Agilent). In the evaluation, only differences in the amounts of transcripts for more than a factor of 2 are indicated for the same total amount of RNA. In FIG. 5 therefore the same brightnesses in the matrix show comparable amounts of transcripts. FIG. 5 shows the amounts of transcripts for sample groups Stabil (composition according to the invention), unbeh (only EDTA added) and T0 (without additive, isolated directly following blood collection) respectively for the samples of donor 1, 2 and 3 at the points of time as indicated.

The aliquots analyzed in FIG. 5 are

| | | donor | | | | |
|---|---|---|---|---|---|---|
| | | 1 | | 2 | | 3 |
| sample | | 1T0 | | 2T0 | | 3T0 |
| sample | 1T1 | 1KT1 | 2T1 | 2KT1 | 3T1 | 3KT1 |
| sample | 1T3 | 1KT3 | 2T3 | 2KT3 | 3T3 | 3KT3 | wherein EDTA-comparative samples are designated with a "K".

The cluster analysis of 199 exemplary selected transcripts, as shown in FIG. 5, clearly shows that the blood samples that were mixed with the composition according to the invention (Stabil) show a comparable pattern of transcripts for a donor at the different points of time of incubation, respectively, while the comparative samples (unbeh) to which only EDTA was added, showed big differences within each donor at the different points of time of the incubation, which indicates an alteration of the amounts of transcripts over time and in view of T0.

For the blood samples to which only EDTA was added, on day 3 compared to day 0 differences in the concentrations were found in 768 transcripts, whereas in the samples to which the composition according to the invention was added, within each donor significantly smaller up to no differences in the concentration of the individual RNAs were found in the samples analyzed at the later points of time in comparison to T0 (see correlation matrix of FIG. 6, comparative samples=K, each at points of time as KT0, KT1, KT3, with the composition according to the invention T0, T1, T3).

By way of the constant amounts of transcripts for individual donors over the time of 3 days in the aliquots of the blood samples mixed with the composition this result shows that the composition of the invention stabilizes the individual RNA molecules from whole blood during the incubation and that the composition, e.g. in comparison to the EDTA comparative samples significantly reduced the degeneration and/or induction of mRNA.

EXAMPLE 4: REVERSE TRANSCRIPTION AND PCR ON THE BASIS OF RNA FROM WHOLE BLOOD

Whole blood originating from two different donors directly following the collection was mixed at 2.5 mL with respectively 6.5 mL of the composition according to the invention of 2.2 M guanidinium thiocyanate, 72 mM MES, 14.4% (wt./vol.) Triton X-100 and 72 mM EDTA in water and incubated at 22.5° C. From these mixtures, aliquots were respectively withdrawn immediately (T0) and after 3 days (T3), after 4 days (T4) and after 5 days (T5) and frozen at −80° C. Subsequently, all samples were thawed in parallel and given onto nucleic acid adsorption agent (NucleoSpin RNA Blood, Macherey-Nagel). The adsorption agent was washed in accordance with the instructions of the manufacturer and the nucleic acids were eluted. To the eluate, DNase (DNase I, RNase free, Article number EN0521, Thermo Fisher Scientific) was added. The RNA was reversely transcribed using the "first strand cDNA synthesis kit" (Article Number K1612, Thermo Fisher Scientific) in order to obtain cDNA. This product was amplified and quantified with primers that were specific nucleotide sequences of the gene for β-actin, GAPDH, IL-8, c-Fos, IL-1B and TNF-α, by means of real-time PCR using the Maxima SYBR Green/ROX qPCR Master Mix (article number #K0222, Thermo Fisher Scientific) in duplicate.

For evaluation, the Ct-values obtained for the cDNA of β-actin and GAPDH were used as an internal standard and to that the Ct-values measured for IL-8, c-Fos, IL-1B and TNF-α were normalized. These relative concentrations of the cDNAs for IL-8, c-Fos, IL-1B and TNF-α at T3, T4 and T5 were additionally related to their respective concentrations at T0. These results are designated as ddCt and in FIG. 7 are shown for the blood of one donor, and in FIG. 8 for the blood of the other donor. The results of both samples make it clear that the composition according to the invention stably maintains the relative concentrations of the specifically detected cellular mRNAs in whole blood over the duration of the incubation at 22.5° C.

The invention claimed is:

1. A method for processing a biological sample, wherein the method is free from reducing agents and the method comprising contacting the biological sample with a composition which functions as a disruption agent for the cells contained in the whole blood biological sample, as a stabilizing agent for total RNA in the whole blood biological sample and as an aqueous solution for isolation by means of adsorption of the RNA from a mixture of the whole blood biological sample and the composition to an adsorption agent for nucleic acids, wherein the composition in aqueous solution is free from reducing agents and consists of:
   a. at least one guanidinium salt,
   b. at least one buffering agent for buffering to a pH of 5.0 to 8.0,
   c. at least one non-ionic detergent and
   d. at least one complexing agent for divalent cations,
   wherein the composition is provided in the mixture in a variable volumetric ratio of the biological sample to the composition of up to 1:13 and the adsorption occurs directly from the mixture in that no component is separated from the mixture, and wherein prior to contacting with the adsorption agent, the nucleic acids are not precipitated and separated from the mixture.

2. The method of claim 1, characterized in that the guanidinium salt is guanidinium thiocyanate, the buffering agent is 2-(N-morpholino) ethanesulfonic acid (MES), Tris (tris(hydroxy methyl)-aminomethane), citrate, phosphate (di-sodium hydrogenphosphate)dihydrate, BisTris buffer (Bis-(2-hydroxy methyl)-imino-tris-(hydroxymethyl)-methane), ACES (N-(2-acetamido)-2-amino methane sulfonic acid), sodium hydrogencarbonate or phosphate-(sodium hydrogen phosphate)dihydrate, the non-ionic detergent is Triton X-100, Tween20, Tween80 (polyoxy ethylene sorbitane monooleate), Brij 58 (poly ethylene glycol-hexadecylether), Triton X-114 (octylphenol polyethylene glycolether) or Nonidet P40 and the complexing agent is ethylene diamine tetraacetate (EDTA) and it is free from thiol compounds or their precursor compounds as reducing agent.

3. The method of claim 1, wherein the method further comprises contacting the mixture with an adsorption agent for nucleic acids, without previous precipitation and separation of nucleic acids by centrifugation of the mixture.

4. The method of claim 1, wherein the composition is contained in a blood collection tube.

5. The method of claim 4, wherein the blood collection tube is adapted to draw in a variable volume of the biological sample.

6. A method for analyzing a blood biological sample, wherein the method is free from reducing agents and the method comprising: collecting blood directly into a blood collection tube, the blood collection tube containing a composition as a disruption agent for cells contained in whole blood, as a stabilizing agent for the total RNA contained in the whole blood and for isolation by means of adsorption of RNA from a mixture of the whole blood and the composition to an adsorption agent for nucleic acids, wherein the blood collection tube is adapted to draw in a variable volume of the biological sample and that the composition in aqueous solution is free from reducing agents and consists of:
   a. at least one guanidinium salt,
   b. at least one buffering agent for buffering to a pH of 5.0 to 8.0,
   c. at least one non-ionic detergent and
   d. at least one complexing agent for divalent cations,
   wherein the composition is provided in the mixture in a variable volumetric ratio of the whole blood to the composition of up to 1:13 and the adsorption occurs directly out of the mixture in that no component is separated from the mixture, and wherein prior to contacting to the adsorption agent the nucleic acids are not precipitated and separated from the mixture.

7. A method for isolating RNA from whole blood, wherein the method is free from reducing agents, the method comprising:
   (i) mixing the whole blood with a composition which in aqueous solution is free of reducing agents and consists of:
      a. at least one guanidinium salt,
      b. at least one buffering agent,
      c. at least one non-ionic detergent and
      d. at least one complexing agent,
      which prevents the degradation and the new synthesis of RNA in whole blood, and thereby producing a mixture which consists of the whole blood and the composition in a volumetric ratio of blood to composition of up to 1:13, optionally with storage of the obtained mixture at above 0° C., optionally with addition of proteinase and/or DNase to the mixture,
   (ii) contacting the mixture with an adsorption agent for nucleic acids, wherein prior to contacting with the adsorption agent no component is separated from the mixture,
   (iii) removing unbound compounds from the adsorption agent, and
   (iv) eluting RNA from the adsorption agent.

8. The method according to claim 7, wherein the contacting of the mixture with the adsorption agent occurs without previous precipitation, separating and dissolving of nucleic acids from the mixture.

9. The method according to claim 7, wherein the storage of the mixture occurs for at least 3 days at maximum 25° C.

10. The method according to claim 7, wherein the mixing of the biological sample and the composition occurs in a volumetric ratio of up to 1:13.

11. The method according to claim 7, wherein the adsorption agent are silica-coated particles, and a thinner is added to the mixture of the biological sample and the composition in a volume of at least 50% of the volume of the mixture.

12. The method of claim 1, wherein a proteinase and/or DNase are added to the mixture.

13. The method of claim 1, wherein the mixing of the biological sample and the composition occurs in a volumetric ratio of up to 1:2.

14. The method of claim 6, wherein a proteinase and/or DNase are added to the mixture.

15. The method of claim 7, wherein a proteinase and/or DNase are added to the mixture.

* * * * *